(12) United States Patent
Garner et al.

(10) Patent No.: US 6,322,565 B1
(45) Date of Patent: Nov. 27, 2001

(54) AVASCULAR NEUCROSIS INSTRUMENT AND METHOD

(76) Inventors: Steven A. Garner, 9204 Trowbridge Cove, Austin, TX (US) 78717; Wayne Gray, 1100 Batavia, Pflugerville, TX (US) 78660; William Reyer, 301 Rolling Green Dr., Austin, TX (US) 78734; Robert Thornberry, 2810 Cline St., Tallahassee, FL (US) 32312

( * ) Notice: Subject to any disclaimer, the term of this patent is extended or adjusted under 35 U.S.C. 154(b) by 0 days.

(21) Appl. No.: 09/436,285

(22) Filed: Nov. 8, 1999

(51) Int. Cl.[7] .................................................. A61B 17/58
(52) U.S. Cl. .............................................. 606/96; 606/101
(58) Field of Search ................................. 606/96, 87, 89, 606/101

(56) References Cited

U.S. PATENT DOCUMENTS 5,409,489   4/1995   Sioufi ........................................ 606/80

OTHER PUBLICATIONS

Aaron, et al., Core Decompression Augmented With Human Decalcified Bone Matrix Graft For Osteonecrosis Of The Femoral Head, Osteoncrosis–Etiology, Diagnosis, and Treatment, American Academy of Orthopaedic Surgeons, Section 9, pp.1–6.

Informational Brochure: DHS/DCS Dynamic Hip and Condylar Screw System, Synthes, pp. 1–28.

*Primary Examiner*—Cary E. O'Connor

(57) ABSTRACT

An avascular neucrosis instrument includes a drill guide member, an extension member attached to an end of the drill guide member, an indexing member attached to the drill guide member, and a flexible drill member extending along the drill guide member and exiting the drill guide member at an angle adjacent the extension member. In another embodiment, the extension is removed from the end of the drill guide member and another extension member is attached to an end of the flexible drill member. As a result, the flexible drill member can be used to form a plurality of channel arrays for the distribution of blood supply to a femoral head.

29 Claims, 5 Drawing Sheets

AVASCULAR NEUCROSIS INSTRUMENT AND METHOD

BACKGROUND

The disclosures herein related generally to surgical instruments and more particularly to an avascular neucrosis instrument and a method of providing a regenerated blood supply to a femoral head.

Osteonecrosis of the femoral head is a progressive disease which involves a disruption of the blood supply causing a portion of the femoral head to die. One surgical approach to treating this disease is core decompression. This involves boring a canal which extends toward the femoral head, filling the bore with bone graft material, and regenerating blood supply to the femoral head via the canal. Various techniques have been used to regenerate blood supply to the femoral head to buy time before a total hip replacement is necessary. These techniques include vascularized and non-vascularized structural bone grafts inserted into the canal, and electric stimulation and osteoinductive grafts which modify the repair response. Decalcified bone matrix (DBM), tamped into the canal, has been shown to be osteoinductive. Other materials may also be suitable.

An important consideration is the effective distribution of the blood supply to the femoral head. The forming of a single canal is helpful but concentrates the regenerated blood supply to a single area or zone at the tip of the canal. This limits exposure of the blood supply to the area immediate adjacent the bore.

Therefore, what is needed is a more effective method of distribution of the blood supply to the femoral head, and a tool for providing an adequate but less concentrated distribution of the blood.

SUMMARY

One embodiment, accordingly, provides an instrument for forming an array of channels for the distribution of the blood supply to the femoral head so that the distribution is dispersed rather than concentrated. To this end, an avascular neucrosis instrument includes a drill guide member, an indexing member attached to the drill guide member, and a flexible drill member extending along the drill guide member and exiting the drill guide member at an angle.

A principal advantage of this embodiment is that an array of channels are provided by indexing the flexible drill member with respect to the drill guide member. As a result of the flexible drill member being indexed and extending at an angle relative to the drill guide member, an array of angled channels are formed to distribute blood supply in a patterned array to the femoral head.

BRIEF DESCRIPTION OF THE DRAWING FIGURES

DETAILED DESCRIPTION

Figure 1:
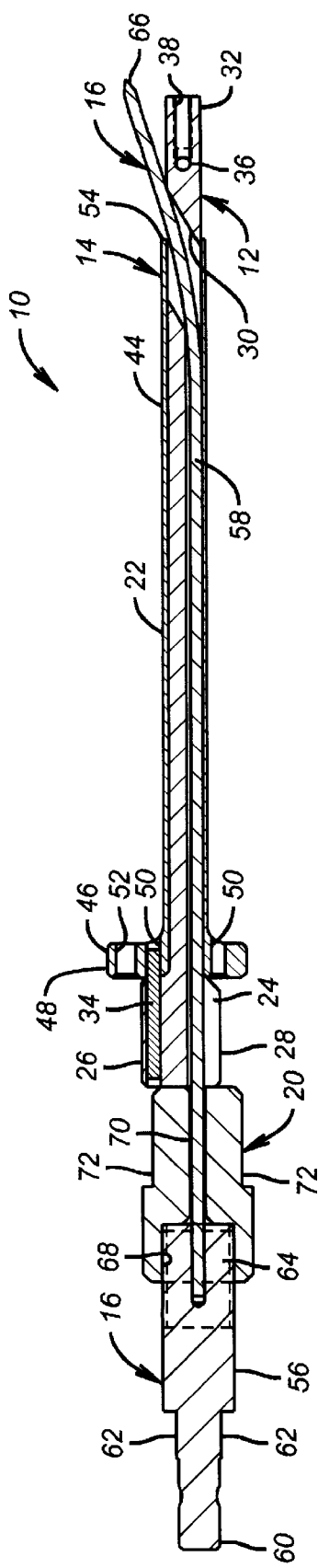
FIG. 1 is a cross-sectional side view illustrating an embodiment of an avascular neucrosis instrument.

An avascular neucrosis instrument is generally designated 10 in FIG. 1. Instrument 10 is usable as a flexible, indexable drilling instrument as will be described in greater detail below. Also, instrument 10 is usable in a first configuration, FIG. 1 and a second alternate configuration, FIG. 2.

Figure 2:
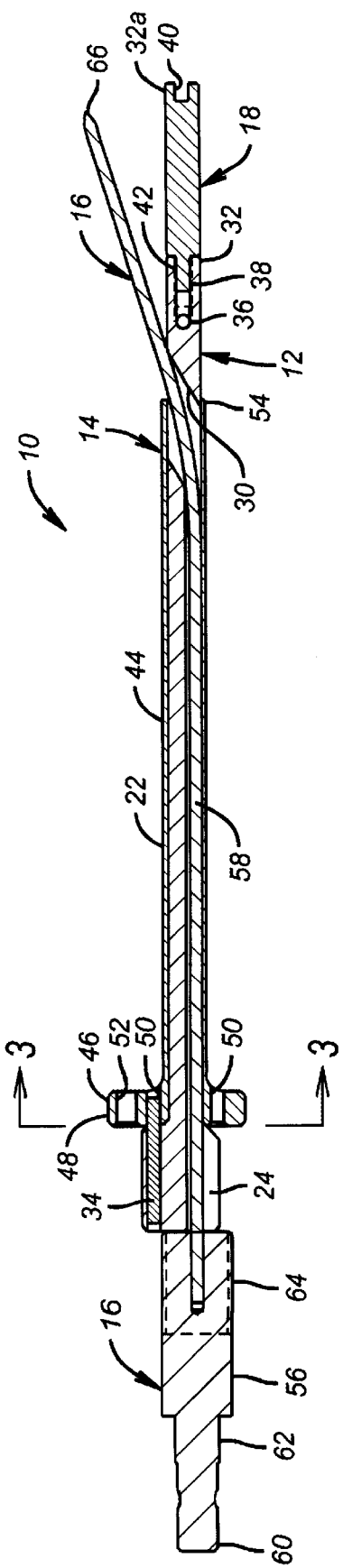
FIG. 2 is a cross-sectional side view illustrating another embodiment of the instrument.

In FIG. 2, instrument 10 includes a drill guide member 12, an indexing member 14, and a flexible drill member 16. An extension member 18 is attached to the drill guide member 12, and alternatively in FIG. 1, a supplemental extension member 20 is attached to the flexible drill member 16.

Drill guide member 12 is an elongated member having an elongated portion 22 including a channel 24 formed therein. If desired, a bore could be formed through portion 22 in place of channel 24. A first end 26 includes a flange 28 attached to elongated portion 22. Channel 24 extends through and along flange 28 and elongated portion 22 and terminates in an angled exit 30 adjacent a second end 32. A key 34 extends from flange 28 at first end 26 for engagement with indexing member 14. Also, drill guide member 12 includes an aperture 36 formed therethrough adjacent second end 32 for receiving a stabilizing member if needed. A threaded aperture 38 extends axially into second end 32 for receiving extension member 18, see FIG. 2. A tool engaging portion such as a slot 40 is provided in an end of extension member 18, and a threaded member 42 is threadable into threaded aperture 38 of drill guide member 12.

Figure 3:
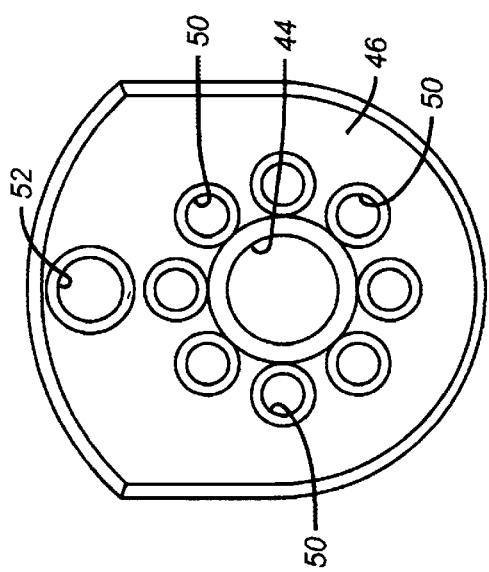
FIG. 3 is an end view illustrating an embodiment of an indexing flange taken along line 3—3 of FIG. 2.

Indexing member 14 is attached to drill guide member 12, FIGS. 1 and 2. Indexing member 14 includes an elongated sleeve 44 for receiving elongated portion 22 of drill guide member 12. A flange 46 at a first end 48 of indexing member 14 includes an array of keyways 50 formed therein, see also FIG. 3. The array of keyways 50 is generally circular. Also, a reference pin aperture 52 is formed in flange 46. When drill guide member 12 is inserted into indexing member 14, second end 32 of drill guide member 12 extends beyond a second end 54 of indexing member 14, see FIGS. 1 and 2.

Figure 4:
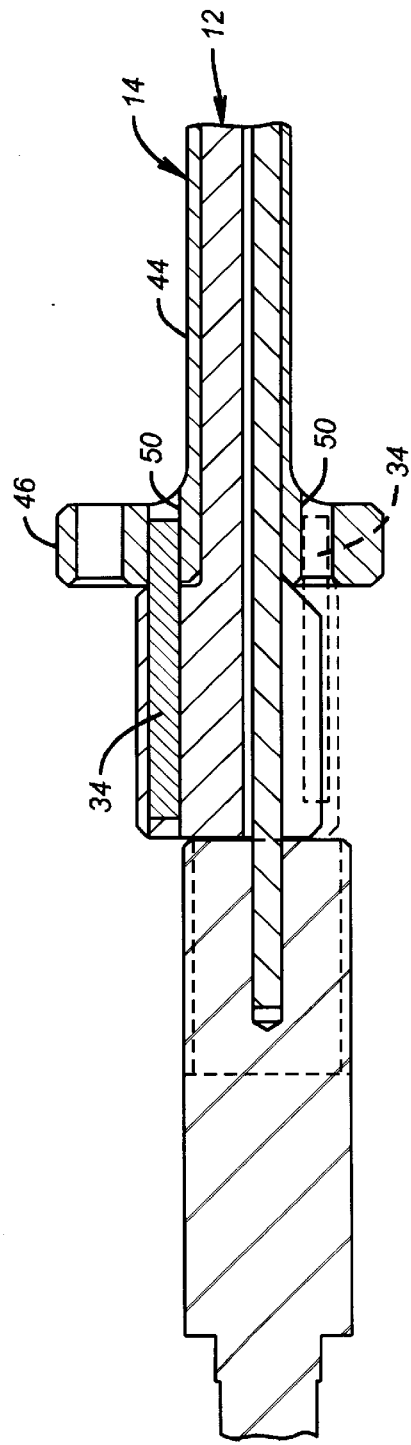
FIG. 4 is a partial cross-sectional side view of the instrument.
Figure 5:
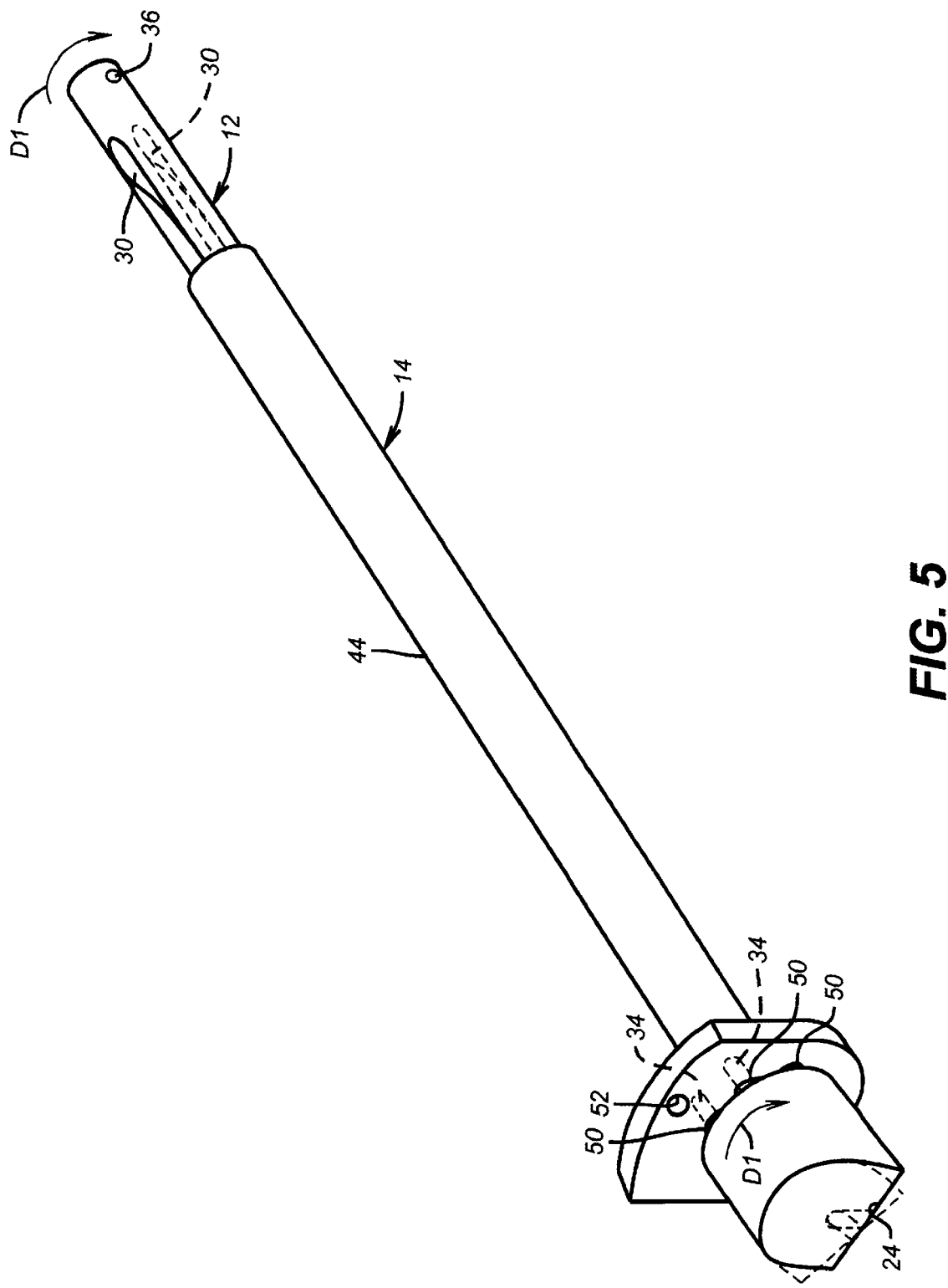
FIG. 5 is a perspective view illustrating an embodiment of indexing positions for the instrument.

Further illustrated in FIG. 4 is the connection of the drill guide member 12 and the indexing member 14. Key 34 is inserted into one of the keyways 50 of flange 46. Drill guide member 12 is rotatable in sleeve 44 so that key 34 can be withdrawn from one keyway 50 and inserted into another keyway 50. This is also illustrated in FIG. 5, which shows drill guide member 12 indexed, or rotated, in sleeve 44 in a direction D1 to move key 34 from one keyway 50 to an adjacent keyway 50. This indexing or rotation also moves the angled exit 30 relative to indexing member 14. As a result, the flexible drilling member 16 can be indexed to various positions for drilling a substantially circular array of channels due to the indexing or rotating of angled exit 30 in direction D1 relative to indexing member 14. Indexing member 14 is maintained in a stationary position due to the insertion of a reference pin (not shown in FIG. 5) in reference pin aperture 52. The reference pin is driven into a bone and fixes the position of the indexing member 14 relative to that bone.

The flexible drill member 16, FIGS. 1 and 2, includes a tool engaging portion 56 and a drilling portion 58. The tool engaging portion 56 includes a first tool engaging portion 60 in the form of a bit head for engagement with a power drilling tool (not shown). A second tool engaging portion is in the form of a pair of opposed flats 62 for engagement by a tool such as a wrench or pliers (not shown). Tool engaging portion 56 also includes a threaded portion 64 for engagement with the supplemental extension member 20, FIG. 1. Drilling portion 58 includes a flexible shaft suitably attached to, and extending from tool engaging portion 56, and is preferably formed of a flexible metal, for example such as a titanium alloy or the product sold under the name Nitinol, or an alloy thereof. A drilling tip 66 is at a terminal end of drilling portion 58.

Channel 24 extends within sleeve 44 and drill guide member 12 is inserted into indexing member 14. Also, key 34 is in one of the keyways 50. A reference pin (not shown in FIG. 1) may be inserted through reference pin aperture 52 and into a bone (not shown in FIG. 1) to fix the position of the indexing member 14 relative to that bone. Flexible drill member 16 may be inserted into drill guide member 12 by inserting drilling portion 58 into channel 24. Drilling tip 66 exits channel 24 via angled exit 30 adjacent second end 32.

In the configuration of FIG. 1, the supplemental extension member 20 includes a tool engaging portion in the form of opposed flats 72, a threaded bore 68 for receiving the threaded portion 64 of flexible drill member 16, and also includes a contiguous bore 70 for permitting drilling portion 58 to extend therethrough and be urged into channel 24 when threaded bore 68 receives threaded portion 64. In this configuration, drilling tip 66 protrudes from angled exit 30 and terminates adjacent second end 32 of drill guide member 12. By indexing channel 24 and thus exit 30 of drill guide member 12 as illustrated in FIG. 5, a first circular array of bores may be formed in a bone by drill member 16.

In configuration of FIG. 2, the supplemental extension member 20 is removed and flexible drill member 16 inserts directly into channel 24 of drill guide member 12. This increases the amount of the flexible shaft of drilling portion 58 which exits drill guide member 12 at angled exit 30 such that drilling tip 66 extends beyond second end 32. The extension member 18 is attached to second end 32 by attachment of threaded member 42 into threaded aperture 38. As a result, drilling tip 66 terminates adjacent extension member 18 which functions to provide a displaced second end 32a. By indexing channel 24 and exit 30 of drill guide member 12 as illustrated in FIG. 5, a second circular array of bores may be formed in a bone by drill member 16. It should be understood that instead of using an extension member, various size drill guide members could be used interchangeably to accomplish the same result.

Figure 6:
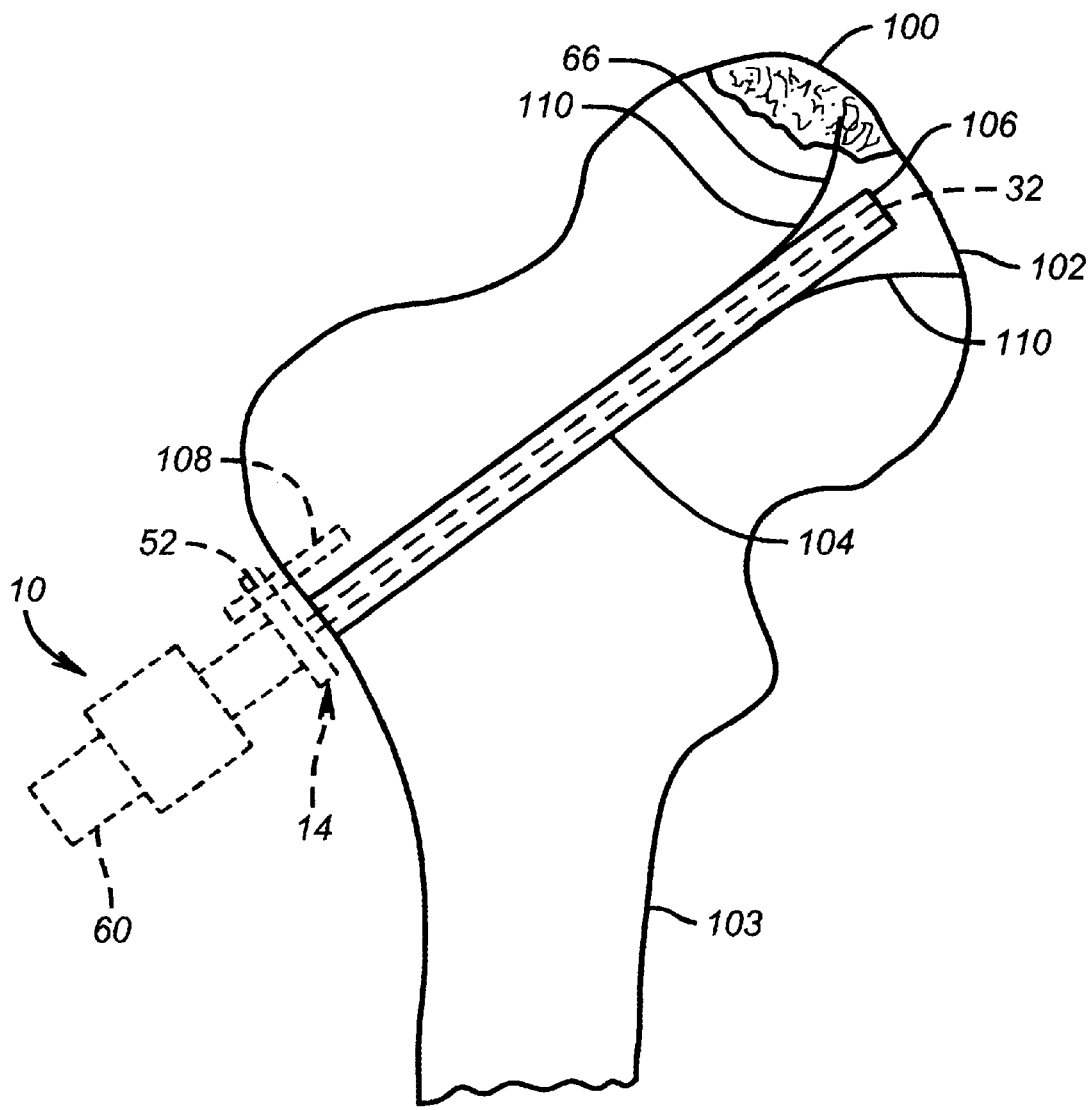
FIG. 6 is a graphical representation illustrating an embodiment of the instrument in use.
Figure 7:
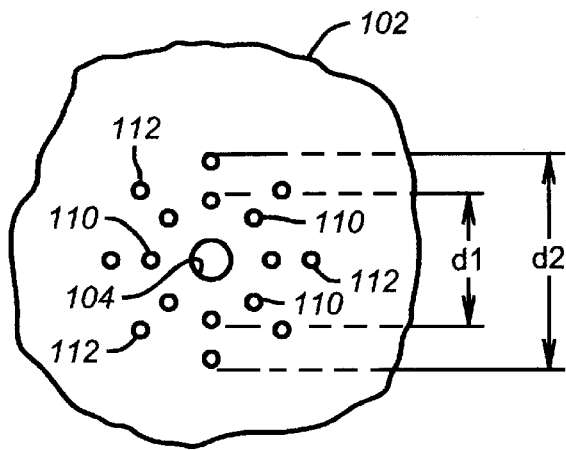
FIG. 7 is a graphical representation illustrating an embodiment of a concentric array of channels formed by the instrument taken along line 7—7 of FIG. 8.

In operation, treatment of osteonecrosis 100, FIG. 6, of a femoral head 102 of a femur 103 is accomplished by boring a canal 104 which terminates at a base 106. Instrument 10 is inserted into canal 104. Instrument 10 may be in either the configuration of FIG. 1 or of FIG. 2. However, assuming that instrument 10 is in the configuration of FIG. 1, instrument 10 is inserted into canal 104 until end 32 seats against base 106. A reference pin 108, FIG. 6, is inserted through aperture 52 to fix the position of indexing member 14 to femur 103. In this configuration, drilling tip 66 terminates adjacent end 32. Attachment of a power drilling tool (not shown) to tool engaging portion 60, drives drilling tip 66 to form a first channel 110 in femoral head 102. By indexing drill guide member 12 within stationary indexing member 14, a first circular array of channels 110 having a first diameter d1, FIG. 7, is formed.

Figure 8:
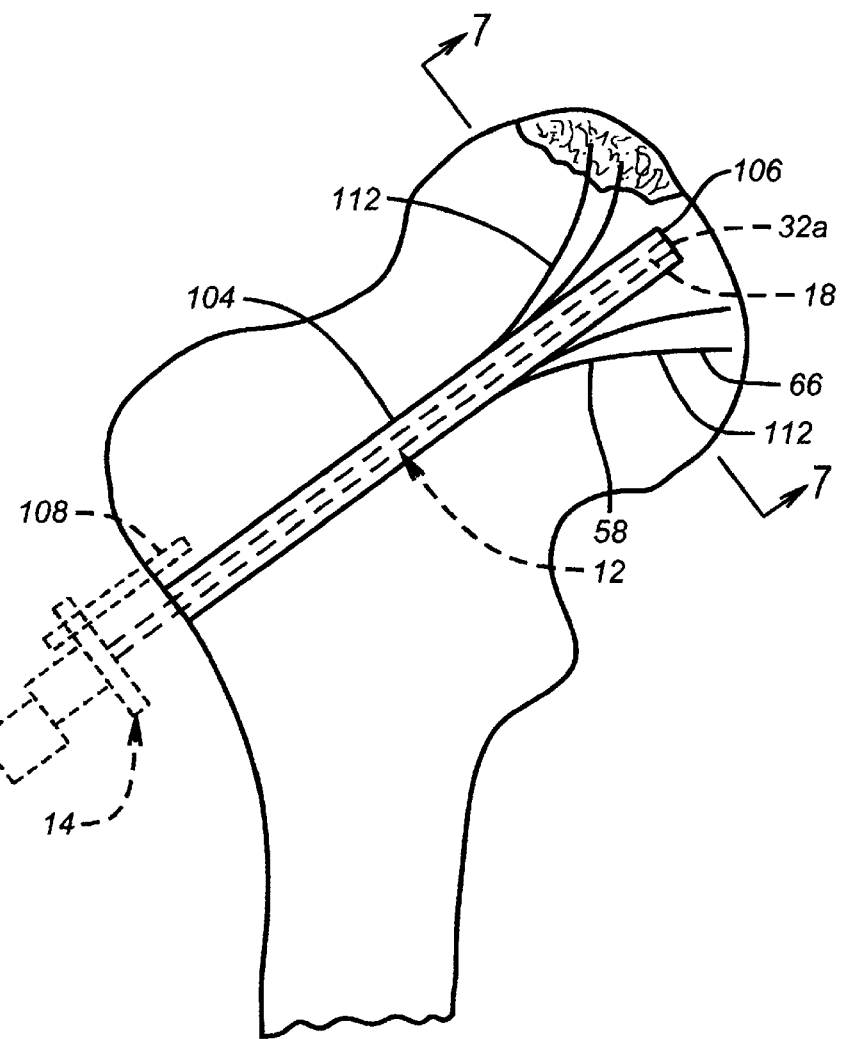
FIG. 8 is another graphical representation illustrating an embodiment of the instrument in use.

Removal of supplemental extension 20, FIG. 8, and attachment of extension 18, seats end 32a against base 106. Therefore, drilling tip 66 terminates adjacent end 32a and an increased amount of the flexible shaft of drilling portion 58 extends from drill guide member 12. Further drilling drives drilling tip 66 to form a second channel 112 in femoral head 102. By indexing drill guide member 12 within stationary indexing member 14, a second circular array of channels 112 having a second diameter d2, FIG. 7, and concentric with first channel array 110, is formed.

As a result, one embodiment provides an avascular neucrosis instrument including a drill guide member, an indexing member attached to the drill guide member, and a flexible drill member extending along the drill guide member and exiting the drill guide member at an angle.

Another embodiment provides a flexible drilling instrument including a drill guide member having a terminal end, an indexing member attached to the drill guide member, a flexible drill member having a driving end and a shaft, the shaft extending along the drill guide member and exiting the drill guide member at an angle adjacent the terminal end, and an extension member attached to the driving end of the flexible drill member.

A further embodiment provides an indexable drilling instrument including a drill guide member, an extension member attached to an end of the drill guide member, an indexing member attached to the drill guide member, and a flexible drill member extending along the drill guide member and exiting the drill guide member at an angle adjacent the extension member.

As it can be seen, the principal advantages of these embodiments are that a multiple array of concentric channels may be provided by indexing the flexible drill member with respect to the drill guide member. As a result of selective placement of an extension member, the flexible drill member being indexed and extending at an angle relative to the drill guide member, and a single array or a multiple array of concentric channels may be formed to distribute blood supply to the femoral head.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. An avascular neucrosis instrument comprising:
    a drill guide member;
    an indexing member attached to the drill guide member; and
    a flexible drill member extending along the drill guide member and bending at one end to exit the drill guide member at an angle.

2. The instrument as defined in claim 1 wherein the drill guide member is an elongated member having an elongated channel formed therein.

3. The instrument as defined in claim 2 wherein the drill guide member includes a key at a first end thereof and an angled opening adjacent a second end thereof, the channel interconnecting the first end and the angled opening.

4. The instrument as defined in claim 3 wherein the indexing member includes an elongated sleeve for receiving the drill guide member.

5. The instrument as defined in claim 4 wherein the indexing member includes an array of keyways at a first end thereof.

6. The instrument as defined in claim 5 wherein the array is circular.

7. The instrument as defined in claim 5 wherein the drill guide member is rotatable in the sleeve for selectively engaging the key with the keyways.

8. The instrument as defined in claim 7 further including an extension member attached to the second end of the drill guide member, whereby the flexible drill member exits adjacent the extension member.

9. The instrument as defined in claim 8 wherein the drill guide member includes an aperture formed therethrough adjacent the second end for receiving a stabilizing member.

10. The instrument as defined in claim 7 wherein the extension member includes a tool engaging portion.

11. The instrument as defined in claim 7 wherein the flexible drill member includes a first tool engaging portion and a second tool engaging portion.

12. The instrument as defined in claim 11 further including a supplemental extension member attached to the flexible drill member.

13. The instrument as define in claim 12 wherein the supplemental extension member includes a tool engaging portion.

14. The instrument as defined in claim 5 wherein the indexing member includes a reference pin aperture formed therethrough.

15. A flexible drilling instrument comprising:
a drill guide member having a terminal end;
an indexing member attached to the drill guide member;
a flexible drill member having a driving end and a shaft, the shaft extending along the drill guide member and exiting the drill guide member at an angle adjacent the terminal end; and
an extension member attached to the driving end of the flexible drill member.

16. The instrument as defined in claim 15 wherein the drill guide member is an elongated member having an elongated channel formed therein.

17. The instrument as defined in claim 16 wherein the drill guide member includes a key at a first end thereof and an angled opening adjacent a second end thereof, the channel interconnecting the first end and the angled opening.

18. The instrument as defined in claim 17 wherein the indexing member includes an elongated sleeve for receiving the drill guide member.

19. The instrument as defined in claim 18 wherein the indexing member includes an array of keyways at a first end thereof.

20. The instrument as defined in claim 19 wherein the drill guide member is rotatable in the sleeve for selectively engaging the key with the keyways.

21. An indexable drilling instrument comprising:
a drill guide member;
an extension member attached to an end of the drill guide member;
an indexing member attached to the drill guide member; and
a flexible drill member extending along the drill guide member and exiting the drill guide member at an angle adjacent the extension member, wherein the drill guide member includes a key at a first end thereof and an angled opening adjacent a second end thereof, the channel interconnecting the first end and the angled opening.

22. The instrument as defined in claim 21 wherein the drill guide member is an elongated member having an elongated channel formed therein.

23. The instrument as defined in claim 22 wherein the indexing member includes an elongated sleeve for receiving the drill guide member.

24. The instrument as defined in claim 23 wherein the indexing member includes an array of keyways at a first end thereof.

25. The instrument as defined in claim 24 wherein the drill guide member is rotatable in the sleeve for selectively engaging the key with the keyways.

26. The instrument as defined in claim 21 wherein the extension member includes a tool engaging portion.

27. A method of drilling a pattern of channels comprising the steps of:
attaching an extension member to a flexible drill member;
connecting a drill guide member to an indexing member in a first indexing position, the drill guide member having an angled exit, the indexing member having an array of indexing positions;
inserting the flexible drill member into the drill guide member so that an end of the flexible drill member exits the drill guide member at an angle adjacent a terminal end of the drill guide member;
drilling a channel;
removing the flexible drill member from the drill guide member; and
repeating the connecting, inserting, drilling and removing steps in sequential indexing positions for forming an array of channels.

28. A method of drilling a pattern of channels comprising the steps of:
attaching an extension member to a drill guide member;
connecting the drill guide member to an indexing member in a first indexing position, the drill guide member having an angled exit, the indexing member having an array of indexing positions;
inserting a flexible drill member into the drill guide member so that an end of the flexible drill member exits the drill guide member at an angle adjacent the extension member;
drilling a channel;
removing the flexible drill member from the drill guide member; and
repeating the connecting, inserting, drilling and removing steps in sequential indexing positions for forming an array of channels.

29. A method of drilling a concentric pattern of channels comprising the steps of:
attaching a first extension member to a flexible drill member;
connecting a drill guide member to an indexing member in a first indexing position, the drill guide member having an angled exit, the indexing member having an array of indexing positions;
inserting the flexible drill member into the drill guide member so that an end of the flexible drill member exits the drill guide member at an angle adjacent a terminal end of the drill guide member;
drilling a channel;
removing the flexible drill member from the drill guide member;
repeating the connecting, inserting, drilling and removing steps in sequential indexing positions for forming a first array of channels;
removing the first extension member;
attaching a second extension member to the drill guide member;

connecting the drill guide member to the indexing member in a first indexing position;

inserting the flexible drill member into the drill guide member so that the end of the flexible drill member exits the drill guide member at an angle adjacent the extension member;

drilling a channel;

removing the flexible drill member from the drill guide member; and repeating the connecting, inserting, drilling and removing steps in sequential indexing positions for forming a second array of channels concentric with the first array of channels.

* * * * *